US010590439B2

(12) United States Patent
Ross et al.

(10) Patent No.: US 10,590,439 B2
(45) Date of Patent: Mar. 17, 2020

(54) ANAEROBIC PROCESS

(71) Applicant: Blaygow Limited, St. Helier (JE)

(72) Inventors: John Morris Ross, Girvan (GB); Cornelius Martin Lynch, Girvan (GB)

(73) Assignee: Blaygow Limited, St. Lawrence (GB)

( * ) Notice: Subject to any disclaimer, the term of this patent is extended or adjusted under 35 U.S.C. 154(b) by 943 days.

(21) Appl. No.: 14/371,855

(22) PCT Filed: Jan. 11, 2013

(86) PCT No.: PCT/GB2013/050046
§ 371 (c)(1),
(2) Date: Jul. 11, 2014

(87) PCT Pub. No.: WO2013/104911
PCT Pub. Date: Jul. 18, 2013

(65) Prior Publication Data
US 2014/0356927 A1    Dec. 4, 2014

(30) Foreign Application Priority Data

Jan. 12, 2012 (GB) .................................. 1200448.7
Jan. 12, 2012 (GB) .................................. 1200463.6
Jan. 12, 2012 (GB) .................................. 1200469.3
Jan. 12, 2012 (GB) .................................. 1200471.9

(51) Int. Cl.
C12P 5/02          (2006.01)
C02F 3/28          (2006.01)
C10L 3/08          (2006.01)
C12F 3/10          (2006.01)
C02F 103/32        (2006.01)

(52) U.S. Cl.
CPC ............... C12P 5/023 (2013.01); C02F 3/28 (2013.01); C02F 3/286 (2013.01); C02F 3/2826 (2013.01); C02F 3/2833 (2013.01); C02F 3/2846 (2013.01); C10L 3/08 (2013.01); C12F 3/10 (2013.01); C02F 2103/32 (2013.01); C02F 2103/325 (2013.01); C02F 2103/327 (2013.01); Y02E 50/343 (2013.01)

(58) Field of Classification Search
None
See application file for complete search history.

(56) References Cited

U.S. PATENT DOCUMENTS

| 4,067,801 A | 1/1978 | Ishida et al. |
| 4,315,823 A | 2/1982 | Witt et al. |
| 4,352,738 A | 10/1982 | Blay et al. |
| 4,415,453 A | 11/1983 | Witt et al. |
| 4,429,043 A | 1/1984 | Paton |
| 5,100,553 A | 3/1992 | Nomura et al. |
| 5,228,995 A | 7/1993 | Stover |

| 2005/0109694 A1* | 5/2005 | You ............ B01D 65/08 210/605 |
| 2006/0060525 A1* | 3/2006 | Hoffland ........ B01D 21/0012 210/603 |
| 2007/0095734 A1 | 5/2007 | Lee |
| 2007/0289921 A1* | 12/2007 | Choi ............... C02F 1/20 210/603 |
| 2009/0280557 A1 | 11/2009 | Ejlertsson |

FOREIGN PATENT DOCUMENTS

| CN | 2143226 | 10/1993 | |
| CN | 1583599 A | 2/2005 | |
| CN | 101023034 A | 8/2007 | |
| CN | 101157937 | 4/2008 | |
| CN | 101195504 | 6/2008 | |
| CN | 101220332 A | 7/2008 | |
| CN | 101265002 | 9/2008 | |
| CN | 101265002 A | 9/2008 | |
| CN | 101280322 A | 10/2008 | |
| CN | 101319230 | 12/2008 | |
| CN | 101541688 A | 9/2009 | |
| CN | 101565719 | 10/2009 | |
| CN | 101805753 | 8/2010 | |
| CN | 101899473 | 12/2010 | |
| DE | 4000834 | 8/1990 | |
| DE | 19717965 | 10/1998 | |
| DE | 19937876 | 3/2001 | |
| DE | 10316680 | 11/2004 | |
| DE | 102005025508 A1 * | 12/2006 | ............. C02F 3/286 |
| DE | 102008015609 | 10/2009 | |
| DE | 202009014905 | 5/2010 | |
| DE | 102009009985 | 8/2010 | |
| EP | 0152730 | 8/1985 | |
| EP | 0414539 | 2/1991 | |
| EP | 1259466 | 11/2002 | |
| EP | 1790732 A1 | 5/2007 | |
| EP | 1792877 | 6/2007 | |
| EP | 1997901 | 12/2008 | |
| EP | 2135938 | 12/2009 | |
| EP | 2226295 | 9/2010 | |
| EP | 2268787 | 1/2011 | |
| EP | 2398743 | 12/2011 | |
| EP | 2419516 | 2/2012 | |
| GB | 2156331 A | 10/1985 | |
| JP | H04-110097 A | 4/1992 | |

(Continued)

OTHER PUBLICATIONS

Britton ("Pilot Scale Struvite Recovery Trials From a Full-Scale Anaerobic Digester Supernatant at the city of Penticton advanced wastewater treatment plant", University of British Columbia, 2002).*

(Continued)

Primary Examiner — Robert J Yamasaki
Assistant Examiner — Charles Zoltan Constantine
(74) Attorney, Agent, or Firm — Beusse Wolter Sanks & Maire; Eugene J. Molinelli

(57) ABSTRACT

The invention relates to processes and equipment for treatment of a feedstock by anaerobic organisms to produce a methane containing biogas that can be used as a source of energy. The invention is particularly concerned with producing methane from a waste plant material such as produced by fermentation processes used in the alcoholic beverages industry, such as from brewing/distilling processes which employ grain material for fermentation.

15 Claims, 4 Drawing Sheets

(56) References Cited

FOREIGN PATENT DOCUMENTS

| JP | H04-300698 | A | 10/1992 |
| JP | H06-246288 | A | 9/1994 |
| JP | 2004-25088 | | 1/2004 |
| JP | 2004-243259 | | 9/2004 |
| JP | 2004298677 | A | 10/2004 |
| JP | 2006-312120 | | 11/2006 |
| JP | 2011-189258 | A | 3/2010 |
| KR | 10-2007-0034556 | | 10/2008 |
| KR | 10-2009-0028147 | | 10/2010 |
| SE | 464520 | | 5/1991 |
| WO | 2006124781 | | 11/2006 |
| WO | 2008108599 | | 9/2008 |
| WO | 2009102142 | | 8/2009 |
| WO | 2009103866 | | 8/2009 |
| WO | 2010120173 | A1 | 10/2010 |
| WO | 2010147928 | | 12/2010 |
| WO | 2011015328 | | 2/2011 |
| WO | 2011066866 | A1 | 6/2011 |
| WO | WO 2011066866 | A1 * | 6/2011 ............ C02F 3/2806 |
| WO | WO2011066866 | A1 | 6/2011 |
| WO | 2011066866 | A1 | 7/2011 |
| WO | 2011107984 | A2 | 9/2011 |
| WO | 2011122056 | | 10/2011 |
| WO | 2011143667 | | 11/2011 |

OTHER PUBLICATIONS

GB Patent Office, "Examination Report for GB1413199.9", dated Sep. 22, 2014, Publisher: GB Patent Office.

C Wen et al., "Domestic Wastewater Treatment Using an Anaerobic Bioreactor Coupled with Membrane Filtration", "Process Biochemistry", Nov. 1999, pp. 335-340, vol. 35, No. 3-4, Published: http://www.sciencedirect.com/science/article/pii/5003295929900076X.

Doyle et al., "Stuvite Formation, Control and Recovery", "Water Research", Sep. 2002, pp. 3924-3940, vol. 36, No. 16, Published: http://144.206.159.178/FT/1092/72646/1241688.pdf.

HHP Fang et al., "Anaerobic Treatment of Brewery Effluent", "Biotechnology Letters", Aug. 1989, pp. 673-678, vol. 11, No. 9, Published: http://link.springercom/article/10.1007/BF01025281#page-1.

Yu et al., "Performance of an Anaerobic Filter Treating Soybean Processing Wastewater With and Without Effluent Recycle", "Process Biochemistry", Jan. 2002, pp. 507-513, vol. 38, Published: hhttp://www.sciencedirect.com/science/article/pii/S0032959202001759.

Kraemer et al., "Continuous Fermentative Hydrogen Production Using a Two-Phase Reactor System with Recycle", "Environ. Sci. Technol.", 2005, pp. 3819-3825, vol. 39, No. 10, Published: http://www.aseanenergy.info/Abstract/31022014.pdf.

Saritpongterraka et al., "Effects of pH Adjustment by Parawood Ash and Effluent Recycle Ratio on the Performance of Anaerobic Baffled Reactors Treating High Sulfate Wastewater", "Bioresource Technology", 2008, pp. 8987-8994, vol. 18, Published: http://www.ncbi.nlm.nih.gov/pubmed/18617396.

Kida et al., "Influence of Mineral Nutrients on High Performance During Anaerobic Treatment of Wastewater from a Beer Brewery", "Journal of Fermentation and Bioengineering", 1991, pp. 54-57, vol. 72, No. 1, Published: http://www.sciencedirect.com/science/article/pii/0922338X91901468.

Loewenthal et al., "Modelling Struvite Precipitation in Anaerobic Treatment Systems", "Water Science and Technology", 1994, pp. 107-116, vol. 30, No. 12, Published: http://www.iwaponline.com/wst/03012/wst030120107.htm.

Melamane et al., "Anaerobic Digestion of Fungally Pre-Treated Wine Distillery Wastewater", "African Journal of Biotechnology", Sep. 2007, pp. 1990-1993, vol. 6, No. 17, Published: http://www.ajol.info/index.php/ajb/article/viewFile/57875/46245.

Li et al., "Anaerobic Treatment of Waste Beer", "Environmental Progress", Aug. 2005, pp. 88-95, vol. 24, No. 1, Published: http://onlinelibrary.wiley.com/doi/10.1002/ep.10041/pdf.

Murray et al., "Effects of Nickel Cobalt, and Molybdenum on Performance of Methanogenic Fixed-Film Reactors", "Applied and Environmental Micorbiology", Sep. 1981, pp. 502-505, vol. 42, No. 3, Published: http://www.ncbi.nlm.nih.gov/pmc/articles/PMC244044/pdf/aem00190-0124.pdf.

Wilkie et al., "Enhancement of Anaerobic Methanogenesis from Napiergrass by Addition of Micronutrients", "Biomass", Jun. 1986, pp. 135-146 vol. 11, No. 2, Published: http://biogas.ifas.ufl.edu/Publs/Biomass-11 (2)135-146(1986).pdf.

Melchior et al., "Biomethanation: Its Future Development and the Influence of the pysiology of Methanogenesis", 1982, pp. 189-197, vol. 32, No. 1, Published: http://www.researchgate.net/publication/230187954_Biomethanation_Its_future_development_and_the_influence_of_the_physiology_of_methanogenesis.

Barlaz et al., Microbial, Chemical and Methane Production Characteristics of Anaerobically Decomposed Refuse With and Without Leachate Recylcing, Jun. 1992 pp. 257-267, vol. 10, No. 3, Published: http://wmr.sagepubs.com/content/10/3/257.abstract.

Baloch et al., "The performance of a Phase Separated Granular Bed Bioreactor Treating Brewery Wastewater", "Bioresource Technology", Jul. 2007, pp. 1849-1855 vol. 96, No. 9, Published: http://www.sciencedirect.com/science/article/pii/S0960852406003361.

Shao et al., "Treatment of Brewery Wastewater Using Anaerob Sequencing Batch Reactor (ASBR)", "Bioresource Technology", May 2008, pp. 3182-3186 vol. 99, No. 8, Published: http://www.ncbi.nlm.nih.gov/pubmed/17659870.

Xuan, J., "Worker Reading of Waste Water Treatment", China Petrochemical Press, Jun. 2004, pp. Summary, 255 and 268, 1st Edition.

Zhijian, C., "Experimental researches for the facilitating effects by the addition of metal ions on the two-phase anaerobic digestion of organic wastes," Engineering Technology, Nov. 15, 2007, pp. 29-37, 1st Edition, Issue 5.

IPO/JP: Office Action, Japanese Patent Application No. 2014-551677, dated Dec. 19, 2016, 6 pages (partial translation).

European Patent Office, "International Search Report for PCT/GB2013/050046", dated Nov. 7, 2013, Publisher: European Patent Office.

Tatara, Mashahiro et al., "High-rate thermophilic methane fermentation on short-chain fatty acids in a down-flow anaerobic packed-bed reactor", "Bioprocess and Biosystems Engineering", Apr. 1, 2005, pp. 105-113, vol. 27, No. 2, Publisher: Springer.

Feng, Xiaoshan, et al. "Anaerobic Digestion Technology". Zhejian Science and Technology Press, first edition, Jul. 1989.

IPO/JP: Office Action, Japanese Patent Application No. 2014-371855, dated Jun. 1, 2018, 13 pages (partial translation).

Nanqi, R., et al. "Principle and Application of Pollution Control Microbiology", (2003), pp. 1-304 (submitted in three parts).

Ronghou, L., "Proceedings of International Seminar on Rural Biomass Energy & ASEAN Plus Three (China, Japan., Korea) Forum on Biomass Energy", 12 pages (2008).

Ronghou, L., et al., "Effects of Temperature on Anaerobic Fermentation for Biogas Production from Cabbage Leaves", 8 pages (2009).

Zhanbin, H., et al., "Enviornmental Biology", 5 pages (2010).

Gavala, H. et al., "Treatment of Dairy Wastewater Using an Upflow Anaerobic Sludge Blanket Reactor", Nov. 5, 1998, pp. 59-63, vol. 73, (May 1999) Issue 1, Publisher: Journal of Agricultural Engineering Research, Published in: https://doi.org/10.1006/jaer.1998.0391.

Goodwin, J., et al., "A further study of the anaerobic biotreatment of malt whiskey distillery pot ale using an UASB system", Bioresource Technology, Dec. 12, 2000, pp. 155-160, vol. 78 (2001), No. 0960-8524, Publisher: Elsevier Applied Science, Published in: https://doi.org/10.1016/S0960-8524(01)00008-6.

ISA/SIPO: First Office Action, Chinese Patent Application #2013800134936, dated Sep. 14, 2015, pp. 1-14, Publisher: The State Intellectual Property of the People's Republic of China.

ISA/GB: Examination Report for Application #GB1413199.9, dated May 21, 2015, pp. 1-3.

Korchef, A. et al., "Phosphate recovery through struvite precipitation by CO2 removal: Effect of magnesium, phosphate and ammonium concentrations", Journal of Hazardous Materials, Nov. 18, 2010, pp. 602-613, vol. 186, 2011, Publisher: Elsevier, Published in: https://doi.org/10.1016/j.jhazmat.2010.11.045.

(56) References Cited

OTHER PUBLICATIONS

Latif, Muhammad, et al., "Integrated application of upflow anaerobic sludge blanket reactor for the treatment of wastewaters", Water Research, Jun. 12, 2011, pp. 4683-4699, vol. 45, (2011), Publisher: Elsevier / Science Direct, Published in: https://doi.org/10.1016/j.watres.2011.05.049.

Agler, Matthew, et al., "Thermophilic Anaerobic Digestion to Increase the Net Energy Balance of Corn Grain Ethanol", Aug. 5, 2008, pp. 6723-6729, vol. 42, No. 17, Publisher: Environmental Science & Technology, Published in: St. Louis, Missouri, USA.

Saidou, H, et al., "Struvite precipitation by the dissolved CO2 degasification technique: Impact of the airflow rate and pH", Nov. 5, 2008, pp. 338-343, vol. 74, Publisher: Chemosphere, Published in: doi:10.1016/j.chemosphere.2008.09.081.

\* cited by examiner

US 10,590,439 B2

ANAEROBIC PROCESS

CROSS-REFERENCE TO RELATED APPLICATIONS

This application is a 371 national stage application of PCT Application No. PCT/GB2013/050046, filed Jan. 11, 2013, and claims the benefit of United Kingdom Application No. GB1200448.7, filed on Jan. 12, 2012; United Kingdom Application No. GB1200463.6, filed on Jan. 12, 2012; United Kingdom Application No. GB1200469.3, filed on Jan. 12, 2012; and United Kingdom Application No. GB1200471.9, filed on Jan. 12, 2012; the entire contents of which are hereby incorporated by reference as if fully set forth herein.

FIELD OF THE INVENTION

The invention relates to processes and equipment for treatment of a feedstock by anaerobic organisms to produce a methane containing biogas that can be used as a source of energy. The invention is particularly concerned with producing methane from a waste plant material such as produced by fermentation processes used in the alcoholic beverages industry, such as from brewing/distilling processes which employ grain material for fermentation.

BACKGROUND TO THE INVENTION

The anaerobic process for the production of biogas (mostly methane and carbon dioxide) is well known. It can be carried out on a continuous basis on waste product streams from a number of industries, typically on aqueous streams including soluble materials derived from plant or animal origin. Such product streams can include suspended solids, to a limited extent; provided they are biodegradable (can be digested in the anaerobic processes). The process can be formally divided into four distinct stages with each stage being carried out by different groups of organisms that in nature can be found together acting in a symbiotic fashion, with the products of one group of organisms being passed on to the next as an energy source (food).

The four distinct phases are:
1. Fermentation and hydrolysis—At this stage the long chain macromolecules present in the effluent solubles stream are broken down to smaller chain molecules. For example in the alcoholic beverages industry there are typically four distinct groups of macromolecule present carbohydrate, protein, oils and fats, and organic acids.
2. Acidogenesis—This involves a group of organisms that produce a broad spectrum of Volatile Fatty Acids (VFA) from the smaller chain substrate produced in (1) above.
3. Acetogenesis—This stage involves the breakdown of VFA to (predominately) acetic acid that becomes the dominant substrate used by a range of methanogenic organisms for the production of methane gas.
4. Methanogenesis—This is the final stage and involves the production of methane gas, together with some carbon dioxide. Typically other products such as ammonia and hydrogen sulphide are also formed.

As an example the aqueous residue from a fermentation and distillation process as used to produce an alcoholic beverage can undergo hydrolysis and acidogenesis relatively easily (at least after removal of the bulk of the undissolved solids content) as the substrate for the organisms concerned is rich in energy and the ratio of macro nutrients (carbon nitrogen and phosphorus—C:N:P) are in an ideal range for these steps, and subsequent methane production.

However, acetogenesis and methanogenesis have proved to be significantly more difficult steps when attempting to provide an efficient process. An efficient process should result in a good removal of organic content (typically measured as a reduction in chemical oxygen demand—COD) and a corresponding high methane content of the biogas.

For example typical anaerobic digestion processes, such as those employed on waste aqueous effluent in the spirits alcoholic beverages industry may only be expected to operate with a COD removal of the order of the order of 70% or less and produce a biogas having a methane content of 70% or less, with the bulk of the remainder being $CO_2$, and so representing carbon that is not available for energy generation. The methane content of the biogas is highly dependent on substrate composition. Substrates that are rich in carbohydrate will typically have lower biogas methane content. Furthermore, additional processing steps typically including aerobic digestion processing are often required to reduce the COD levels to those acceptable for disposal e.g. to drain.

In U.S. Pat. No. 6,395,173 (Von Nordenskjold—now known as BIOLAK Technology GmbH) an anaerobic treatment apparatus is described that can be used for treatment of "waste waters". It is suggested the apparatus is suitable for waste waters having a biological oxygen demand (BOD) in excess of 2000 $mgl^{-1}$. Such a BOD may equate to a COD of about 4000 $mgl^{-1}$ depending on the source of the organic content and represents a relatively dilute waste stream to be treated. The apparatus includes a two stage sludge bed, of the upflow anaerobic sludge blanket reactor (UASB) type, wherein sludge and liquid effluent from the reactor can be recycled. As is common with waste water treatments an aerobic treatment stage can be applied to the liquid effluent post the anaerobic stage to complete the reduction of COD. A similar option is suggested for dealing with excess sludge. However, waste waters of about 4000 $mgl^{-1}$ may be considered to be relatively weak and adapting the apparatus and process for digesting waste streams of higher COD concentration is not as straightforward as it may seem. Typically users may consider diluting the liquid waste stream prior to introducing this to the methanogenic apparatus, but such dilution has potentially undesirable consequences in terms of flow rates through the apparatus, hydraulic retention time, maintaining alkalinity and/or conversion rates.

Moreover the waste water may be acidic in pH, particularly when initially subjected to an acidogenesis/acetogenesis step, although many waste waters are naturally acidic. Such acidic pH may have a significant detrimental effect on methanogenesis which is preferably carried out in slightly alkaline conditions. In view of this, many prior art processes control pH through the addition of alkali, such as lime. Saritpongteeraka, K and Chaipratpat, S. (Bioresource Technology 99, (2008) p 8987-8994) describe a process in which pH is controlled through addition of NaOH or parawood ash. This process is carried out in an anaerobic baffled reactor with and without effluent recycle. Their results appear to show pH control is essential, but that effluent recycle has little effect. Nevertheless, the influent COD was typically in the rate of 5000-6500 mg/l and although a long hydraulic retention time was suggested as being of benefit, this was at the expense of the organic loading rate.

Although the above process did not suggest that effluent recycle was of benefit, this is in fact routinely adopted and proposed for use in fluidised bed and UASB reactors treating carbohydrate rich waste waters to make use of alkalinity generated internally and to dilute the influent COD (see Sam-Soon, P., Water S A, 1991; 17(1): p 37-46 and Ferguson J F, Water Research, 1984:18(4) 573-80). Such recycling and its benefits, particularly when employing high COD waste streams is also discussed in U.S. Pat. No. 4,415,453.

It is an object of the present invention to provide methods and apparatus for carrying out an anaerobic digestion of a waste stream that avoids or at least reduces one of the aforementioned problems.

DESCRIPTION OF THE INVENTION

According to a first aspect the present invention provides a process for the anaerobic digestion of a substantially aqueous solution, or aqueous and oil two phase system, which has a COD concentration of 30 to 130 $kgm^{-3}$, comprising the step of subjecting the substantially aqueous solution, or aqueous and oil two phase system to a methanogenic stage, in order that methanogenic organisms produce methane by digestion of organic material in the substantially aqueous solution, or aqueous and oil two phase system and wherein a liquid output from the methanogenic stage is recycled at no more than a ratio of 2:1 of recycled liquid:input substantially aqueous solution, or aqueous and oil two phase system and wherein the COD of an output stream from the methanogenic stage is reduced by more than 70% from the input substantially aqueous solution, or aqueous and oil two phase system.

The process will typically be a continuous process, for efficient throughput and utilisation of equipment. The liquid output from the methanogenic stage may be recycled at no more than a ratio of 1:1 or even without recycle. The COD reduction may be for example more than 80% or even from 90% to 95% or more relative to the input.

The process according to the first aspect of the invention provides a high level of reduction of COD, and therefore can avoid the need for an aerobic treatment post the methanogenic stage as is commonly used for waste water treatments in order to reduce the COD content sufficiently to allow ready disposal e.g. to drain. However where consent limits for disposal of effluent are strict a small aerobic treatment may be employed to reduce the COD left after the methanogenic stage even further. In general the process produces an exceptional reduction of COD together with a good quality biogas containing useful amounts of methane. The liquid output can also find use e.g. as a fertiliser.

The recycling of the liquid output from a methanogenic stage as described herein refers to the conventional practice of returning a portion of the liquid output from a methanogenic stage to the input location (and therefore high COD concentration area) of the methanogenic part of the anaerobic process. The recycled liquid can be fed into the methanogenic process together with the input aqueous effluent stream or through a separate inlet or inlets. In either case the recycled liquid enters the process vessel or vessels at or near where the COD concentration is high and acts to dilute the input aqueous effluent stream. Note, this is not to be confused with solids/sludge recycling which is also known in the art.

According to a second aspect the present invention provides a process for the anaerobic digestion of a substantially aqueous spirit distillation effluent stream, which has a COD concentration of 30 to 130 $kgm^{-3}$, comprising the step of subjecting the substantially aqueous solution, to a methanogenic stage, in order that methanogenic organisms produce methane by digestion of organic material in the substantially aqueous solution, and wherein a Liquid output from the methanogenic stage is recycled at no more than a ratio of 2:1 of recycled liquid:input substantially aqueous solution, and wherein the COD of an output stream from the methanogenic stage is reduced by more than 70% from the input substantially aqueous solution.

As with the first aspect of the invention the process will typically be a continuous process, for efficient throughput and utilisation of equipment. The liquid output from the methanogenic stage may be recycled at no more than a ratio of 1:1 or even without recycle. The COD reduction may be for example more than 80% or even from 90% to 95% or more relative to the input.

As with the process according to the first aspect an aerobic finishing process is not required to produce good results in terms of COD reduction. Furthermore the effluent from the methanogenic stage can provide useful products as described hereafter.

According to a third aspect the present invention provides a method of processing a liquid material, the process comprising subjecting the liquid material to an anaerobic digestion process for example as described herein; and monitoring the content of at least one micronutrient, in particular at least one micronutrient metal in a methanogenic stage of the anaerobic process wherein methanogenic organisms produce methane by digestion of organic compounds present in the liquid material and may utilise said at least one micronutrient; in order that an amount of said at least one micronutrient may be added to the methanogenic stage in response to the results of the monitoring.

The monitoring of micronutrient levels and addition of micronutrients to a methanogenic stage may be carried out as part of an anaerobic process according to the first or second aspects of the invention, or more generally for other anaerobic processes. Typically the anaerobic process will be a continuous process. Procedures for monitoring are described with reference to some examples hereafter.

More preferably monitoring of at least one micronutrient is conducted on the influent to the methanogenic stage and the effluent from the methanogenic stage, whilst taking account of potential sludge growth. In this manner it is possible to determine whether or not micronutrients present in the influent are bio-available and hence capable of being used to facilitate growth of the microorganisms in the sludge and hence how much additional micronutrient may be added to facilitate growth, but not so much as to have any potential toxic effect.

The fermentation and hydrolysis, acidogenesis and acetogenesis stages of the overall processes according to the first, second or third aspects of the invention may be carried out in the conventional manner. Typically, an "acidogenic" reactor is employed wherein at least some of the fermentation and hydrolysis, acidogenesis and acetogenesis stages are carried out, in advance of the methanogenic stage. Such a reactor typically runs at acid pH in the range of 3.5 to 5. A pH in the range of 3.5 to 4.2 has been found to assist in allowing acetogenesis to occur, thereby enhancing levels of VFAs passed forwards to the subsequent methanogenic stage, however in practice a methanogenic stage has been shown to be capable of processing VFAs i.e. acetogenesis occurs to produce acetic or other small chain carboxylic acids.

In summary the methanogenic stage makes use of anaerobic microorganisms that produce methane but other stages of the overall process e.g. acetogenesis can occur in the methanogenic stage.

If required the feed (substantially aqueous solution, aqueous and oil two phase system, substantially aqueous spirit distillation effluent stream or liquid material) may adjusted to an acid pH as required before it is processed in the acidogenic reactor. In general, where an acidogenic reactor is employed (at least for a spirits drinks effluent stream) the acidogenic process is relatively fast with a typical hydraulic retention time of only circa 24 hours (with no recycling). Typically the acidogenic stage is carried out with mixing in the reactor. Typically and advantageously 90% or more of the acetogenesis stage is carried out early in the process i.e. in the acidogenic reactor, as this reduces the potential for poor activity in the subsequent methanogenic stage caused e.g. by slow conversion to acetic acid.

Suitable high COD concentration feedstocks for use in the processes include the effluent stream from a spirit drinks production process, in accordance with the second aspect of the invention. After fermentation and distillation of the alcohol produced, the spent grain or other vegetable mass is filtered off (for example by means of centrifuges or other filtration techniques) and the remaining solution is processed. The resulting solution may include a limited quantity of suspended solids such as spent yeast cells, depending on the filtration technique employed. Such aqueous effluent streams may be those produced by any of the typical spirits drinks production processes e.g. those for whisky, gin, vodka, rum, brandy, bourbon, tequila etc. Other suitable feedstocks can include whey from cheese manufacture, molasses or molasses diluted with water or other aqueous system, and vegetable oils. Vegetable oils may be processed by addition to an aqueous system, even though they form a two phase system. Mixtures of feedstocks may be employed. In a preferred embodiment, the process described herein may find particular application in treating malted barley and/or grain whisky waste water. Example waste water streams from malt/grain whisky production are shown in FIGS. 2, 3 and 4. Other suitable high COD concentration feedstocks may be envisaged, such as from vegetable, such as soy, beet, potato processing and the like.

For some substrates, such as whey, the feedstock may arrive at the anaerobic process at ambient temperature. However the microorganisms employed are generally mesophilic or alternatively thermophilic. Therefore the effluent stream or other feedstock being treated may be heated e.g. in the range of about 30° C. to 37° C. for mesophilic bacteria, as required. Heat generated from combustion of the biogas produced in the anaerobic process may be employed for this purpose.

Typically the feedstock for the anaerobic digestion is substantially a solution, i.e. contains organic and other species derived from natural products, in solution. However some suspended solids can be present, provided they do not interfere with the continuous process. Suspended solids can be tolerated if they can be digested by the anaerobic process e.g. yeast cells from a fermentation process used to make an alcoholic beverage. The amount of suspended solids (as yeast) that can be tolerated from a spirits drinks process can be up to about 15,000 mgl$^{-1}$ or even higher. A typical maximum solids amount is 2%, 3% or 4% w/w of solid: liquid. Yeast is about 46% (dry basis) protein and consequently the nitrogen from the protein can increase the amount of ammonia in the effluent from the anaerobic reactor. For example by some 15 to 20%. Conversely suspended solids that take a long time to be digested, particularly those with high cellulose or lignin content, are not readily processed and may require a long time residence time, 20 days or more.

The anaerobic processes according to the first and second aspects of the invention operate at a high Chemical Oxygen Demand (COD) input concentration. Conventionally examples of anaerobic processes applied to aqueous effluent streams of soluble components operating as continuous processes may have an input COD concentration of for example, about 5 kgm$^{-3}$ to 25 kgm$^{-3}$ or higher but with a substantial recycle to dilute the input concentration as discussed further herein. The process of the present invention can operate with input COD concentrations of the order of 30 kgm$^{-3}$ or more, or even 35 kgm$^{-3}$ or more, without recycle or with minimal recycle. Typically a high COD concentration in the range of 40 kgm$^{-3}$ to 130 kgm$^{-3}$ may be successfully employed.

Advantageously the liquid output from the methanogenic stage is not recycled. However there may be recycle of some of the solids, typically the sludge containing the microorganism mass that can be carried out of a vessel employed for the methanogenic stage. This sludge will contain a limited amount of the liquid output, depending on the separation equipment and method employed, but will generally be insignificant where a methanogenic stage is being operated with no deliberate recycle of the liquid output.

Preferably the methanogenic process is carried out in an enclosed tank or lagoon containing a sludge bed of microorganisms fed by an upwards flow. Preferably the process is carried out by a so called up flow anaerobic sludge blanket reactor (UASB) although others typically called anaerobic lagoons, fluidised bed, packed bed and hybrid digesters may also employed. However, it should be appreciated that advantageously the reactors of the present invention are not actively stirred or only employ anaerobic filters, which would either increase costs and/or reduce COD levels which can be applied. Such reactors are typically operated on a continuous basis. In such a reactor the input, typically from an acidogenic reactor, is fed upwardly into a sludge bed, including methanogenic microorganisms, contained within the sludge/UASB. The input feedstock is pumped in at several locations towards the input end of the sludge/UASB. As digestion proceeds (reduction of the COD concentration and generation of biogas) the liquid in the tank flows towards the output end of the reactor where a reduced COD liquid effluent is removed. Operating a reactor UASB with the process of the invention, where no or a limited recycle of the liquid output is applied is thus done under limited mixing conditions, with the input injection into the sludge bed providing limited agitation, in comparison with a high recycle method where large volumes of liquid and/or sludge are removed from the reactor and reinjected into the sludge bed, at or near the input area or in a process where active stirring with a motor is employed.

The methanogenic process may be carried out in stages, for example in two or more tanks in series or a divided tank as described hereafter with reference to a specific embodiment. Preferably less than 4 stages, typically less than 3, such as 2 stages are employed. Multiple stages of processing allow a sludge bed with a high COD input to be followed by a sludge bed with a low COD input as a finishing or "polishing" methanogenic stage. Remarkably when such a two stage methanogenic sludge bed is operated with a process according to the invention it has been found appropriate to provide an input of the aqueous effluent stream into the low COD input sludge bed, in order to maintain the health of the microorganisms contained within. The process of the invention achieves such a high reduction in COD in the first stage that the second stage is starved of the required amount of feed. Thus the process may be operated in smaller reactor volumes than expected for conventional procedures.

Alternative reactors include packed bed reactors or mixed reactors (typically with stirring or agitation by gas injection). Although the methanogenic stage reactor or reactors are fed from a preceding "acidogenic" reactor where one or more of fermentation, hydrolysis, acidogenesis and acetogenesis occurs, it will be understood that acetogenesis or other processes may occur within the reactor or reactors involved in the methanogenic stage.

The liquid effluent contains organic material not converted to methane or other gases such as $CO_2$, ammonia and very minor quantities of $H_2S$. By not recycling this output in the conventional manner substantial benefits may be obtained.

Typical recycle of effluent from the methanogenic stage is substantial in prior art processes, within the range of between 3:1 and 12:1. (That is 3 of recycle to 1 of input stream; up to 12 of recycle to 1 of input stream—by volume).

The intent of such a recycle is to dilute the COD concentration present at the input end of the reactor, assist in adjusting the pH and allow the opportunity for unreacted material in the effluent to be converted to methane. The dilution of the COD concentration entering the methanogenic stage is typically regarded as an essential feature if a reasonable process efficiency (for a given process volume) is to be achieved. Retention times ("hydraulic retention times") are often given for anaerobic digesters as a measure of flow of fluid through the system. The high recycle rates typically used in prior art processes result in lower hydraulic retention times in comparison with the hydraulic retention times of the present process. The retention time is calculated on the basis of the process volume (i.e. volume of the methanogenic stage reactor contents) divided by the flow through per day, including the recycle volume that is returned to the reactor. For the processes of the present invention a retention time of the order of 5 to 15 days, typically of 8 to 12 days, for example of 10 days may be successfully employed. This contrasts with retention times of, for example, 1 to 3 days where a high recycle is used. Such low retention times increase the likelihood of loss of microorganism mass from the methanogenic phase (loss of sludge).

Surprisingly removal or reduction of the recycle has been shown to allow a high COD concentration input as discussed above. The throughput expressed as kg of COD per of reacting mass (volume of sludge and liquid in the methanogenic reactor or reactors) per day i.e. the COD in $kgm^{-3}$ $day^{-1}$ remains good, for example from 3 kg even up to and beyond 5 kg COD $m^{-3}$ $day^{-1}$. At the same time the efficiency is high, providing both a high level of COD removal and a high quality biogas (high methane content). Remember the methane content is linked to the substrate composition. High oil—high methane conversely high carbohydrate lower methane percentage.

For example a COD removal of 90% or more, generally the range of 80% to 95% can be achieved. At the same time the biogas can be obtained with high methane content, more than 70%, typically 75% to 80%. (I am inclined to make this 58-80%—this then takes account of substrates dominated by carbohydrates) A yield of the order of 0.35 $m^3$ methane (at standard temperature and pressure) per kg of COD removed can be obtained. As the processes produce an exceptionally high reduction of COD, the yield of biogas produced is correspondingly high. In conjunction with these benefits a high level of bicarbonate alkalinity has been shown to be generated within the reactor carrying out the methanogenic stage. This high level of bicarbonate alkalinity (typically 4000 to 5000 $mgl^{-1}$, expressed in terms of $mgl^{-1}$ of calcium carbonate), is obtained naturally without supplementation and itself provides notable benefits.

The bicarbonate alkalinity can be calculated as follows:

Bicarbonate alkalinity (as $mgl^{-1}$ calcium carbonate)= Total Alkalinity($mgl^{-1}$ $CaCO_3$)−Total Volatile Fatty Acids (ppm)×0.71

The total alkalinity is determined by titration to pH 4.0 using 0.1 N hydrochloric acid. Total alkalinity is made up of carbonate, bicarbonate and alkaline alkalinity. However, the presence of the bicarbonate ion is important to the removal of the inhibitory propionic acid. The total Volatile Fatty Acids is determined by gas chromatography. See also "Biological Wastewater treatment, Vol 4, Anaerobic Reactors", 2007, Carlos Augusto de Lemos Chernicharo, published by IWA publishing, London.

High bicarbonate levels tend to reduce the build up of inhibitory levels of byproducts such as propionic acid in the reactor. This contrasts with a process run with a conventional recycle level, especially when the COD concentration of the input is high. Propionic acid levels (and the level of other undesired species such as ammonia) have been found to be significant and bicarbonate levels correspondingly low where a recycle is operated. Such conditions result in much reduced quality of biogas and reduced COD removal in comparison with the process of the present invention. The conventional approach to such reduced COD removal and poor quality biogas would be to increase the recycle rate even further in an attempt to afford more opportunity for the microorganisms to consume COD and/or to reduce the concentration of COD in the input.

Furthermore, with a natural high bicarbonate alkalinity the methanogenic stage readily maintains the desirable pH (7.2 to 7.4) because of the very large reservoir of alkalinity present in the reactor. This can avoid any requirement to adjust pH with added alkalinity. Adjustment of pH is conventionally required or at least desirable when operating a methanogenic stage as the input from a preceding acidogenic reactor will have a low pH e.g. at about 3.5. Advantageously, the present inventors have observed that alkali material is only required during an initial start up of a reactor, typically for between 7 to 21 days until the required level of bicarbonate alkalinity has developed in the reactor. Thereafter, further addition of alkali or pH control may/is not (be) required, saving on costs and efficiency. Moreover, the reactor is stable to the introduction of acidic, high COD waste streams.

A further additional advantageous feature of the high bicarbonate alkalinity is in relation to struvite production (as will be described in more detail hereinafter). Whilst in the methanogenic stage, only relatively small amounts of crystallised or precipitated struvite is produced. However, upon exiting from the methanogenic stage, a reduction in a partial overpressure is observed, when the output stream contacts atmospheric pressure, which allows for $CO_2$ to be released from solution, with a consequential increase in pH (typically greater than about 0.2-0.3 pH units), which results in the struvite substantially spontaneously precipitating from solution and/or microcrystals agglomerating.

Further benefits of not recycling include the reduction of the build up of ammonia which reduces the process efficiency and can lead to problems of effluent disposal.

The liquid effluent from a process of the invention, for example utilising a vegetation based aqueous effluent stream as feed (such as from a spirits drinks production process), can be of sufficient quality to meet local consent limits for disposal to drain. Furthermore the liquid effluent from the anaerobic digestion can provide useful by products.

As discussed in more detail hereafter and with reference to a specific embodiment from a spirits drinks effluent digestion, such as waste water from malt and/or grain spirit distillation process the liquid effluent issuing from a methanogenic stage operated in accordance with the invention can spontaneously produce crystals of the mineral struvite ($NH_4MgPO_4.6H_2O$). The unwanted production of struvite causing blockage of pipes and other equipment is a known problem for sewage and other solids waste disposal facilities. However in accordance with the present invention struvite production, as discrete crystals, can be obtained. The present inventors noticed that struvite can be produced and appropriately collected for subsequent use. As mentioned above, only relatively small amounts of struvite, in terms of a precipitable form, may be produced during the methanogenic phase, but upon output from the methanogenic phase large quantities of precipitated or agglomerated struvite may be observed. Without wishing to be bound by theory, it is thought that at least partly due to the relatively high bicarbonate alkalinity, most of any struvite which is produced in the methanogenic phase remains in solution or in a fine microcrystalline form. However, upon exiting from the methanogenic phase, $CO_2$ gas evolves from the output stream, which results in an increase in pH of the solution and precipitation/agglomeration of the struvite present.

Upon exiting from the methanogenic phase and precipitation from solution, the struvite produced in this fashion may be readily removed from the liquid by use of a suitable filtration technique (for example by hydrocyclones). However, in order to prevent the struvite from clogging or blocking any pipe-work or conduits, the present inventors have found it desirable to employ flexible tubing/pipes, in order to prevent a build up of the struvite on the walls of the tubes/pipes and hence help minimise clogging.

The collected struvite can find use as a fertiliser. Even after struvite removal the remaining liquid effluent contains nitrogen potassium and phosphorus in a suitable ratio for use as fertiliser and so can be processed further for that purpose if desired. The processing of the liquid effluent may include evaporation to a concentrate for use as a liquid or evaporation to a solid product e.g. by spray drying.

The processing of the feed in the methanogenic stage requires a stable, healthy and productive microorganism mass. In addition to the removal or at least reduction of the recycle discussed above, other improvements to a methanogenic process may be made.

As far as the third aspect of the invention is concerned it has been found that additions of micronutrients, especially at least one metal salt comprising one or more of cobalt, nickel, and iron, at levels in excess of the expected requirement can also produce significant benefits. Selenium may also be employed as an added micronutrient. Other micronutrients such as vitamins, for example riboflavin, vitamin B12 may be appropriate depending on the input to an anaerobic process. With an aqueous stream derived from a spirits drinks process riboflavin may already be present in sufficient quantity. Advantageously a salt of each of cobalt, nickel and iron is added, with selenium also added as required. Typically metal salts are provided in the form of a chloride salt.

It has been found that improvements in maintenance of the biomass and in the quality of the process output are achieved by monitoring the micronutrient content, preferably by an accurate analytical method, such as ICP—(inductively coupled plasma mass spectroscopy) and adding measured amounts of micronutrients. Both the monitoring and/or the additions of the micronutrients may be done automatically if desired. Monitoring can avoid overdosing of a micronutrient, some of which are toxic to anaerobic microorganisms when in excess.

Other monitoring of a methanogenic stage can be advantageous, for example using an Oxidation-Reduction Potential probe (ORP probe) to measure oxidation-reduction potential within the methanogenic stage. This measurement provides indication that the process is operating correctly in an anaerobic fashion. Typically if the measurement is of the order of −350 mV to −400 mV then the process is operating in favourable conditions. If the measurement drifts from such a value then less favourable conditions for the production of methane are present.

As far as the measurement of micronutrient content is concerned it may be made following obtaining samples (manually or automatically) from the methanogenic stage itself. Advantageously and conveniently the monitoring of the content of a micronutrient in a methanogenic stage is not determined from sampling the content of the methanogenic stage itself but is determined by measuring the micronutrient level in the input to the process or to the methanogenic stage and also in the output from the methanogenic stage and comparing the two results in conjunction with an understanding of the expected growth of microorganisms in an efficiently operating process.

When operating a methanogenic stage of an anaerobic process, for example, an anaerobic process with a feed from a spirits drinks process, it has been found that the levels of measured micronutrient in the input and in the output can be comparable in content, indicating that the micronutrient in the feed is not readily bio-available to the microorganisms, which would be expected to consume the micronutrient as they grow, reducing the amount found in the liquid output. For this reason adding micronutrients as a supplement, typically on a daily or weekly basis in response to monitoring results, has been found beneficial. With a smoothly running process and a relatively consistent feed the monitoring steps do not need to be carried out frequently, but additions on a daily or weekly basis keeps the micronutrient levels within the desired concentrations. Continuous 24 hour dosing may be employed rather than addition on a batch basis.

Thus according to a fourth aspect the present invention provides a method of monitoring the micronutrient requirement, in particular the requirement for metal micronutrients, in a methanogenic stage of an anaerobic digestion process, such as described herein wherein methanogenic organisms produce methane, the method comprising:
  measuring the amount of at least one micronutrient in the feed to the process or in the feed to a methanogenic stage of the process;
  measuring the amount of the same at least one micronutrient in the effluent from the process or from the methanogenic stage of the process; and
  estimating the amount of the at least one micronutrient to be added to the methanogenic stage to sustain growth of microorganisms in the methanogenic stage based on the difference between the amount in the feed and the amount in the effluent and on the expected growth of the microorganisms in the methanogenic stage.

The process monitored may be a continuous process.

Typical "target" amounts of micronutrients can be found in the literature for anaerobic sludges, for example the metals required to sustain a healthy culture of microorganisms. For example, Iron—1,800 mg kg$^{-1}$. Nickel—100 mg kg$^{-1}$ and Cobalt—75 mg kg$^{-1}$. (on a dry weight of sludge basis). For selenium smaller amounts are indicated, typically less than 50 mg kg$^{-1}$.

An example calculation based on the typical iron figure shown above is now given.

The growth of new anaerobic sludge each day is estimated. This is done by calculating the growth rate by obtaining samples from the sludge (typically by sampling from various locations within the sludge bed and drying the samples). Maximum and minimum growth rates may be obtained by measuring sludge when the process is providing a high COD reduction and when it is providing a low COD reduction. In practice the calculation is performed assuming a high growth rate is occurring in the sludge. In the example the following figures were measured and calculated for a process employing separate acidogenic and methanogenic stages. Where a consistent feed to the anaerobic process is employed these figures may be expected to remain approximately constant.

Maximum Methanogenic Stage Sludge Growth per day=0.05 kgs anaerobic sludge (dry weight) per kg COD removed.

Minimum Methanogenic Stage Sludge Growth per day=0.02 kgs anaerobic sludge per kg COD removed.

The COD removal quoted is on the basis of a methanogenic stage having allowed for the COD reduction found in the acidogenic stage.

Assume one methanogenic stage reactor is supplied with 30,000 kgs COD per day and 90% of this is removed.

That means sludge growth=30,000×0.9×0.05 kgs=1,350 kgs sludge per day.

If on monitoring, the feed and anaerobic effluent iron levels are approximately equal, then the sludge is not consuming the iron provided by the feed (lack of bioavailablility of the iron in the feed).

Therefore each kg of sludge still requires 1,800 mg iron.

If the input or indeed effluent streams is/are monitored alone, and the value was in excess of 1,800 mg/kg then it may have incorrectly been assumed that there was insufficient iron, but this does not take account of whether or not it is bio-available.

Therefore the supplementation requirement is 1,800 mg×1,350 kgs=2430 grams of iron (as metal) per day. This is a minimum—in practice slightly more is used as some of the added iron will be not available for use by the microorganisms e.g. because it binds to sulphur. The iron required would typically be added in the form of a salt, typically as ferric chloride. Similar calculations/measurements may be made on other metals.

If on monitoring the sludge was shown to be consuming iron in the feed—the effluent from the anaerobic process contains less iron than the input feed—then a lower supplementation rate may be applied, as some of the iron for growth is being provided by the feed. However, higher than the calculated amounts may be used to determine if greater growth of microorganisms can be achieved, perhaps allowing greater throughput. In general a slight excess of micronutrient can be employed. With such a dosage regime, when operating a robust consistent process, monitoring of the output liquid will tend to show a slight elevation of iron in comparison to the input, indicating that sufficient iron is being supplied.

This dosing of the methanogenic organisms with micronutrients can be used with a process according to the first or second aspect of the invention or other embodiments but is not restricted for use with such processes.

Other treatments may be beneficial.

Dosing with aluminium chloride may also be employed to control the growth of filamentous organisms, which if present in excess can result in the sludge being more cohesive, leading to severe foaming. For this purpose aluminium chloride is added at prescribed levels determined by the filamentous index (a count of the number of filamentous organisms). If these organisms are not controlled then a bulking sludge (similar to a mousse) may form at the liquid—gas interface of the methanogenic phase.

Yet further improvement to methanogenic processes, including to a methanogenic process according to the first aspect of the invention may be obtained by avoiding loss of the microorganism mass. In normal operation of, for example an upflow anaerobic sludge blanket reactor (UASB), some sludge is displaced from the reactor by the flow through of the process stream. This normal (relatively small) quantity of displaced sludge is separated out from the liquid effluent, for example in a lamella separator and returned to the methanogenic reactor. However on occasion substantial quantities of the sludge containing the microorganisms may be displaced out of the tank or other vessel employed and into the liquid effluent as a consequence of foaming or other disruption of the sludge blanket caused by gas generation in the sludge bed that is not smoothly released. The deleterious loss of sludge can be prevented by the addition of a suitable quantity of an iron salt, for example iron III chloride (ferric chloride). Appropriate levels of iron salt are of the order suggested above as appropriate for supplying iron as a micronutrient and therefore added iron can serve a dual purpose.

Thus according to a yet further aspect the present invention provides a method of reducing loss of microorganism mass from a methanogenic anaerobic process comprising addition of iron, for example in the form of a salt such as iron III chloride.

A starter culture of microorganisms for carrying out an anaerobic digestion may be obtained commercially, from suppliers operating conventional anaerobic processes, such as sewage sludge treatments. On application of the process conditions the culture of microorganisms becomes adapted, with organisms finding the conditions advantageous growing at the expense of those finding the conditions adverse. Once the process has been run for a period of time, typically at least a few weeks or months, the sludge is stably adopted for use in digesting the same or similar feedstock.

For the stages carried out before the methanogenic stage appropriate microorganisms can be found ubiquitously in the environment, especially in the (nutrient rich) aqueous effluent streams contemplated as feedstock for spirits drinks processes which can produce rapid growth of these organisms e.g. 0.15 kg per kg of COD removed. Thus a reactor carrying out the preliminary fermentation, hydrolysis, acidogenesis and/or acetogenesis steps does not normally require a starter culture of organisms.

For the methanogenic stage a starter loading of microorganisms can be obtained, for example from an anaerobic digestion system employed to treat solid wastes in sewage works operations. Such sources provide a sludge containing mesophilic bacteria, which become conditioned by the feedstock and operating conditions to provide a stable collection of microorganisms efficiently producing the high quality outputs discussed above. The conditioning will naturally result in the reduction or death of bacteria types not capable of efficiently utilising the feedstock as an energy source and the increase in populations of bacteria that can make use of the feedstock as an energy source. The mesophilic bacteria operate best at temperature of the order of 35° C. to 40° C., typically at about 37° C. The desired temperature can be maintained within the methanogenic stage by use of suitable heating systems in the known manner, if required.

DETAILED DESCRIPTION OF THE INVENTION WITH REFERENCE TO THE DRAWINGS AND SPECIFIC EMBODIMENTS

The invention will now be further described with reference to specific embodiments and the accompanying drawings.

The processing of an aqueous effluent stream containing soluble organic components derived from a distillery operation is now described. After fermentation of a water/grain mixture and distillation to remove the alcohol content, the aqueous waste was separated from solids (both spent grain and yeast were removed, typically by the use of filter presses, in this example).

Figure 2:
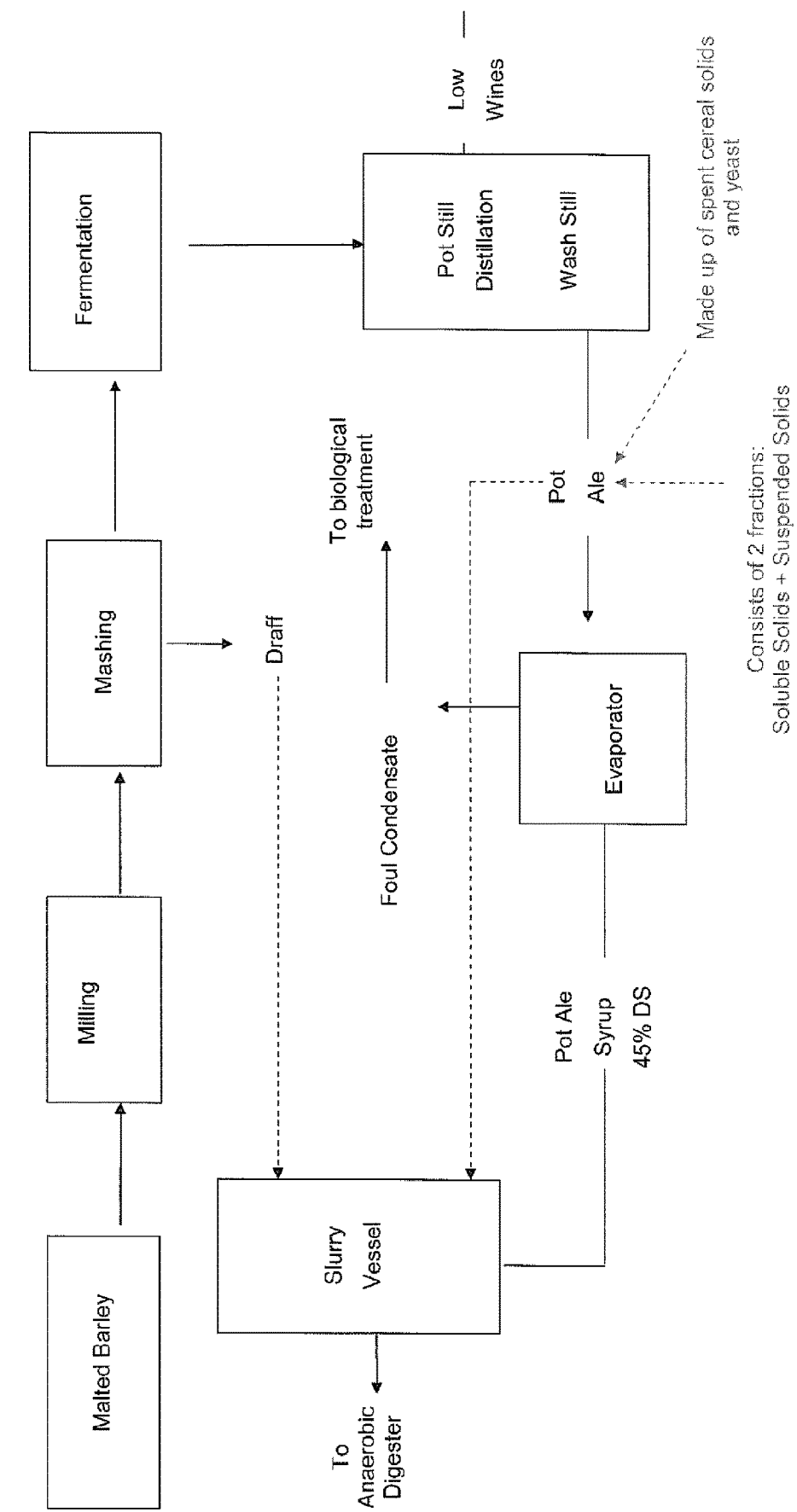
FIGS. 2-4 show schematic flow diagrams of grain and malt whisky distillation processes and the waste liquid streams which are generated and may be subjected to anaerobic digestion in accordance with the present invention.

A typical composition of the aqueous grain distilling effluent stream is shown in Table 1 below. This is the soluble solids liquid stream as shown in FIG. 2. The data is based on a distillery operating with an alcohol fermentation process that operates with 65 to 70 degrees original gravity.

Figure 3:
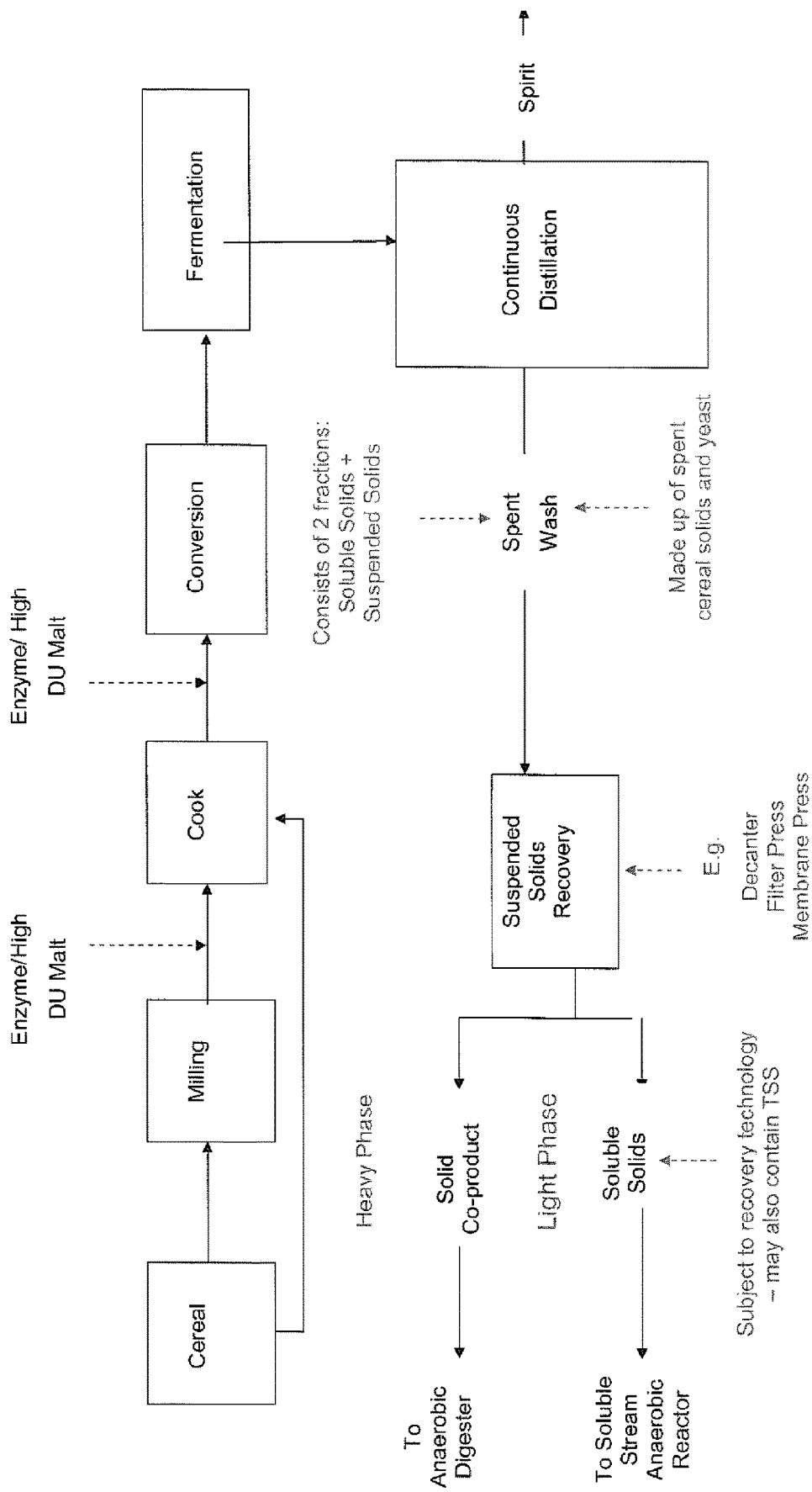
Figure 4:
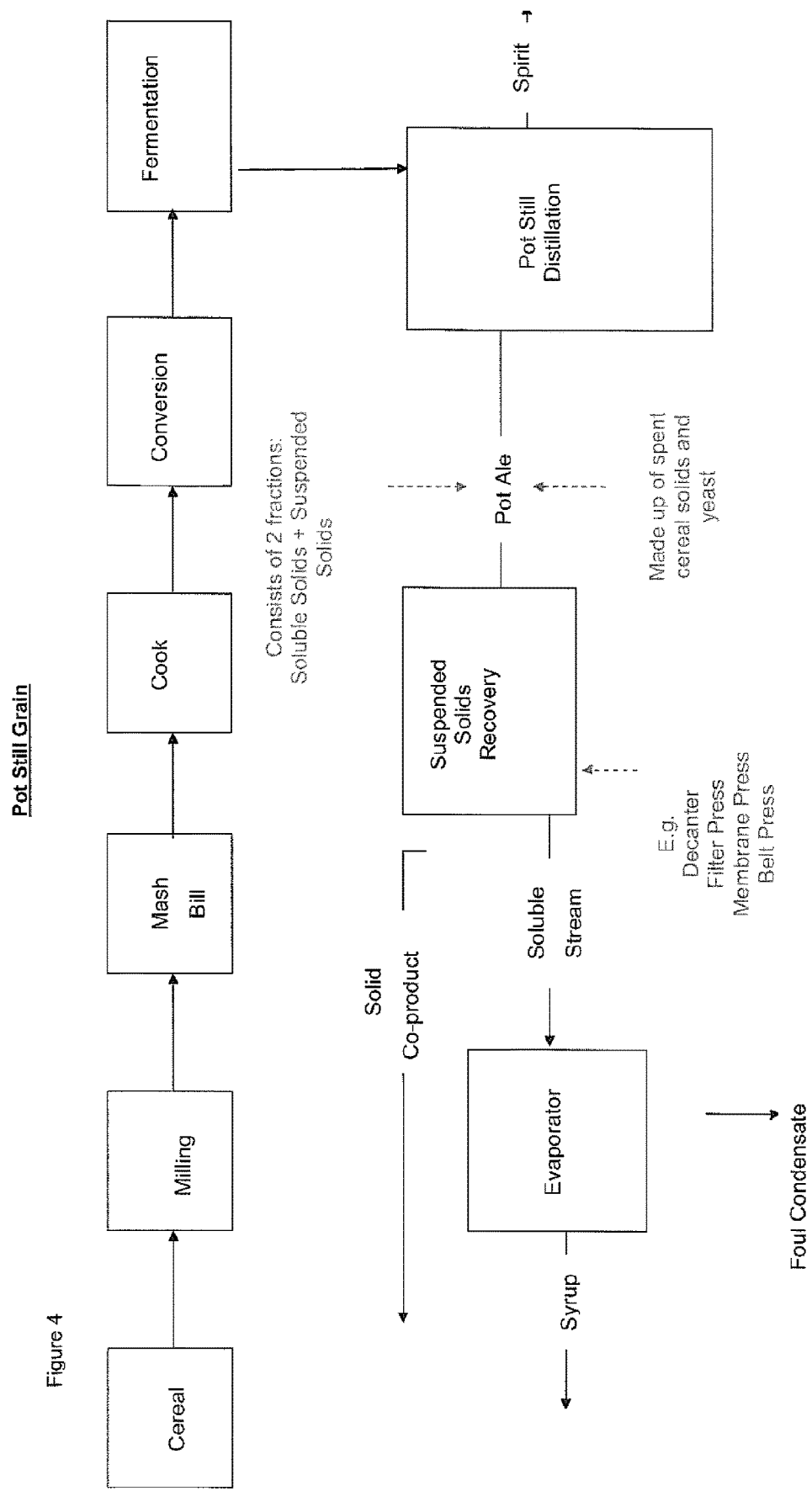

FIGS. 3 and 4 show alternative liquid streams (pot ale and/or pot ale syrup) which may be employed in the process according to the present invention.

TABLE 1

| No. | Distillery Soluble Effluent Stream | Value |
|---|---|---|
| a | Light straw colour with cooked cereal nose. | — |
| 1 | Chemical Oxygen Demand | 40,000 mg/l |
| 2 | Biological Oxygen Demand | 20,000 mg/l |
| 3 | pH Range (natural) | 3.7-4.2 |
| 4 | Temperature of Feed to Acidogenic Reactor- deg C. | 38 deg C. |
| 5 | Total Solids | 5.0% |
| 6 | Total Suspended Solids | 0.25% |
| 7 | Suspended Solids Type | Trace cereal solids, yeast cells |
| 8 | Dissolved Solids | 4.75% |
| 9 | Dissolved Solids Type | Organic, Trace Mineral Ash |
| 10 | Dissolved Solids Breakdown - Typical Compositional Data Expressed as % on dry basis; Typical ranges as +/−5 to 10%. | Protein - Circa. 15% Carbohydrate - Circa. 70% Oil - Circa. 3% Organic Acids - Circa. 1% Glycerol - Circa. 3% Magnesium 250 mg/l Ammonium 60 mg/l Phosphate 300 mg/l Sulphur, 3 mg/l |

Figure 1:
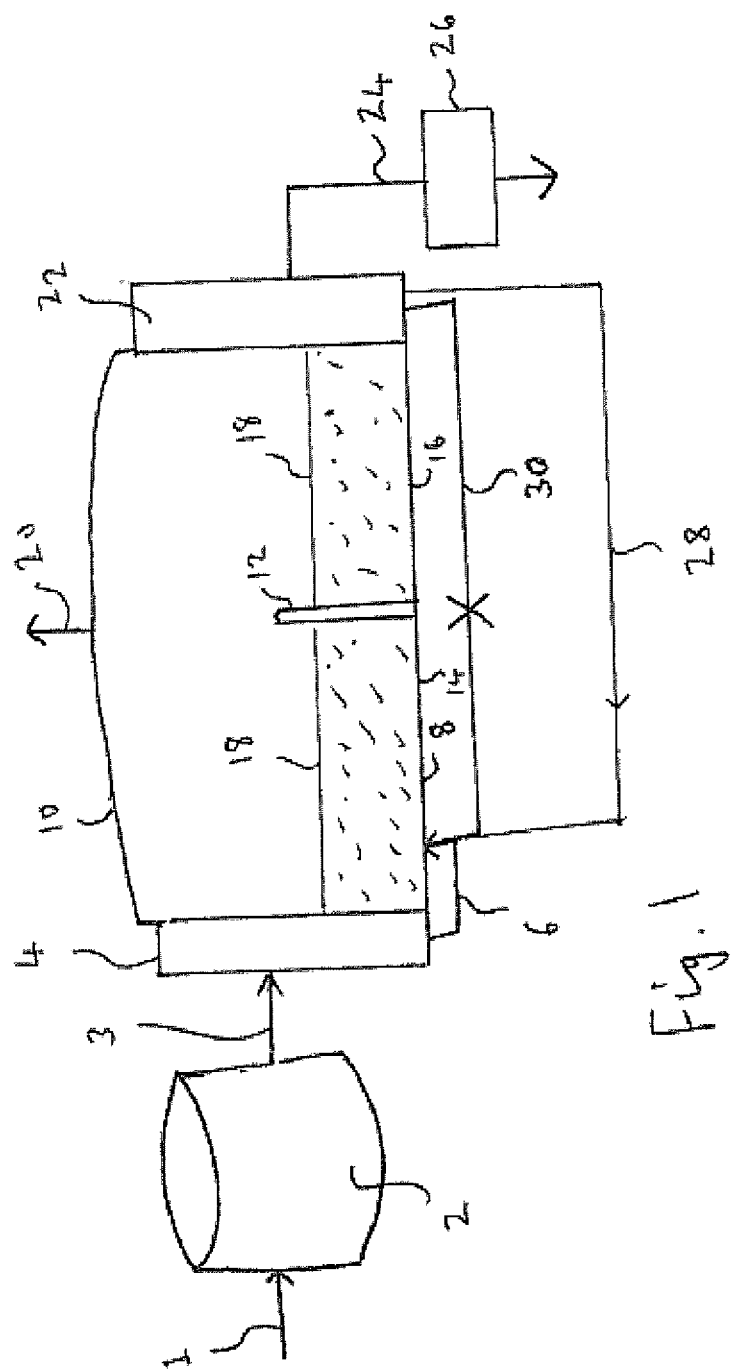
FIG. 1 illustrates schematically the operation of an anaerobic digestion process.

FIG. 1 shows schematically an apparatus suitable for a continuous anaerobic digestion process in accordance with the present invention. The apparatus can be of the form described in more detail in U.S. Pat. No. 6,395,173.

An apparatus of this form was supplied for the digestion of a liquid of the type described in Table 1 above.

The methanogenic stage has a process volume of about 8,700 m³. The hydraulic retention time in the methanogenic stage was expected to be of the order of 3 days as a significant recycle was anticipated as a requirement by the suppliers of the reactor. The preceding acidogenic process volume was 720 m³, giving a hydraulic retention time of the order of 24 hrs for that stage (no recycle is applied to the acidogenic stage).

When operating in conventional fashion with a substantial recycle the apparatus had a design loading of 3.5 kg CODm⁻³day⁻¹. In operation 70% of this COD loading was expected to be removed by the conventional process and the resultant biogas was expected to have a methane content of 60-75%.

In practice when using a conventional level of recycle and without metals additions the process did not perform well. A high level of propionic acid was found in the recycling fluid and low natural bicarbonate alkalinity (typically, a negligible amount) was found in the methanogenic stage. At the same time the conversion of COD was poor and the quality of biogas a measured by methane content was also lowered. Thus operating as planned resulted in low efficiency.

For example, during a period where a recycle stream was applied at 6:1 the propionic acid levels in the recycle were high (1-3 kgm⁻³) and consequently had an inhibitory effect on the methanogenic stage of the anaerobic process. This recycle steam also contributes to the COD loading (methanogenic phase COD loading=COD from feed+COD from recycle stream). This combined flow (recycle and feed) also has an impact on the hydraulic retention time as discussed previously.

COD breakdown and methane content of the biogas were generally low, both in the region of 65-70%.

During operations with this recycle it was noted that there was no bi-carbonate alkalinity present in the reactor.

The conventional response when poor performance such as this is found would be to increase the recycle or decrease the feed concentration, with a resulting loss in process throughput. However increasing the recycle even up to 12:1 did not improve the COD removal.

Surprisingly once the recycle was reduced and ultimately stopped, to follow the process of the invention, a number of fundamental changes were observed. Bi-carbonate alkalinity rose rapidly to >4,000 mgl⁻¹, and the propionic acid levels in the output from the reactor reduced to less than 100 mg/litre. Improved COD reduction, better quality biogas and struvite crystallisation were also observed. The applicant is currently running 3 reactors in such a fashion and producing approximately 17,500 m³ biogas per day per reactor. This is equivalent to 11,300 m³ methane per day at a 65% methane amount in the biogas. The biogas produced is used to run two Jenbacher gas engines, which produce a total of 150 MW of electricity per day. These reactors have been run non-stop continuously for since 2009. It is expected that more gas and electricity could be generated, but the current limitation is the amount of feed available to provide to the generators, currently approximately 45 tonnes of COD is being removed per reactor per day As shown in FIG. 1, in operation in accordance with the invention, an aqueous waste stream feed 1, for example similar to that of table 1 above is passed into a balance tank 2 which provides a buffer volume of input to the anaerobic process and can smooth out inconsistencies in the output from upstream processes.

The balance tank 2 serves as a buffer volume as it can allow the process to continue even if the feed 1 is interrupted or intermittent. The output 3 from the balance tank 2 (of the order of 50 m³ per hour) then enters an "acidogenic" tank 4 containing organisms where volatile fatty acids are produced and then broken down to acetic acid. The output 6 from the tank 4 (at a pH of the order of 3.5) is the input for a large two stage methanogenic process tank 8 which may be of concrete construction covered by a flexible sheet gas hood 10. Typically the process tank 8 will be buried or partially buried in the earth.

The process tank 8 is configured to operate as an upflow anaerobic sludge blanket reactor (UASB), in this example with two stages.

The UASB 8 is divided by a wall 12 (having passages for fluid to pass through) into two subunits, a high COD load first subunit 14 and a low COD load second subunit. A sludge blanket of methanogenic organisms 18 is provided in each sub unit 14,16 of the tank 8.

In practice the output 6 from the acidogenic/acetogenic stage is fed upwards at several locations into tank 8 as in a conventional process at the input end of the tank i.e. into the high COD load first unit 14 (multiple inputs not shown for clarity). Baffles may be provided in the first unit 14 to aid mixing. Some of output 6 (generally a small amount) may also be fed to the low COD subunit, to maintain health of the microorganisms contained within which may be otherwise starved. The microorganisms in sludge blanket 18 digest the input 6 producing a biogas 20 containing 75% to 85% methane with the remainder being mostly $CO_2$ with small amounts of $H_2S$ and ammonia. The biogas 20 can be purified (removal of the sulphur component) and then used as fuel, for example in a gas engine connected to a generator to produce electricity. Waste heat from the exhaust gases may in turn be used, for example to generate useful steam energy.

The input 6 to UASB 8 flows gradually through, exiting via lamella separator 22 as an effluent stream 24 that can be discharged to drain following some minor clarification procedures, that may include removal of struvite. The struvite produced tends to crystallise out of the effluent stream 24 after it exits the lamella separator 22 possibly due to a raising in pH. Removal of struvite may be for example by use of one or more hydrocyclone separators indicated by box 26 placed before discharge to drain. Struvite production of some 2.5 tonnes per day can be realised in the described system using a feed similar to that in table 1, with the limiting factor to struvite production being input of magnesium from the feed. The lamella separator is used in the known manner to separate sludge carried out of tank 8 by the flow through of the process stream. The wet sludge from the lamella separator is normally returned to the tank 8, via a return line 28.

The process described above differs from the conventional procedure by not recycling liquid effluent 24 at a high ratio (conventionally 3:1 to 12:1) via recycle line 30 for liquid from the lamella separator 22. In some circumstances a limited recycle may be employed, at up to 1:1 or even 2:1.

The addition of metals, typically iron cobalt and nickel was shown to aid in COD removal and biogas production, the benefit being of the order of 10-15% of COD removal and the equivalent methane production equating to 350 m³ per tonne COD removed at STP. The metals addition was carried out in accordance with the third and fourth aspects of the invention as discussed above. The overall health of the sludge bed and robustness of the process was also improved.

When operated as described above the process has been found to be stable and robust with a COD removal level of the order of 90% to 95%. The biogas quality is high, typically 60% to 75% methane. Other notable features of a process operated in this manner include:

A loading rate of 5 kg's COD $m^{-3}$ $day^{-1}$ or more can be used;

A natural high pH (7.2-7.4) consequent to a natural high bicarbonate level (>4000 mg per litre) that can be maintained without adjustment;

The inhibitory propionic acid is absent or remains in low concentration (<50 $mgl^{-1}$).

Further Example

Pilot plant and laboratory scale reactors of the upward flow anaerobic sludge blanket types were used to study the anaerobic digestion of whey.

The digestion was carried out in two stages using separate acidogenic and methanogenic reactors. The reactors were of the cylindrical tower style.

The whey was obtained from a local source and had a COD of circa 80,000 mg per litre.

The COD loading rate was of the order of 5 $m^{-3}$ $day^{-1}$ or slightly more.

When the anaerobic process was operated with typical recycle the COD removal was of the order of 75%.

When the anaerobic process was operated without recycle a COD removal of the order of 80% was achieved with a methane yield of 0.33 m³ methane per kg of COD removed.

The above tests were carried out without the addition of metals.

The invention claimed is:

1. A process for the anaerobic digestion of a substantially aqueous solution or an aqueous and oil two phase system containing organic material to produce a liquid output wherein the COD is reduced by more than 70% from the input COD, comprising:
   providing a feed of a substantially aqueous solution or aqueous and oil two phase system that has a COD concentration of 40 to 130 kg/m³ to an enclosed tank or lagoon containing a sludge bed of methanogenic microorganisms via an upward flow;
   subjecting the substantially aqueous solution, or aqueous and oil two phase system to methanogenesis to produce methane by digestion of the organic material in the enclosed tank or lagoon, wherein the liquid output from the enclosed tank or lagoon is not recycled in the process;
   producing a liquid output from the enclosed tank or lagoon with a COD reduced by more than 70% from the input COD;
   monitoring the content of at least one micronutrient in the feed and in the liquid output; and,
   adding the at least one micronutrient when the difference in micronutrient level between the feed and the liquid output is less than expected based on the amount of methane produced and the expected growth of the methanogenic microorganisms.

2. The process according to claim 1 wherein the substantially aqueous solution or aqueous and oil two phase system is a substantially aqueous spirit distillation effluent stream.

3. The process according to claim 1 wherein the substantially aqueous solution or aqueous and oil two phase system is a solution/system from cheese manufacture, sugar production, or vegetable processing.

4. The process according to claim 1 wherein the process is a continuous process.

5. The process according to claim 1 wherein the COD of the liquid output from the enclosed tank or lagoon is reduced by 90% or more relative to the input.

6. The process according to claim 1 wherein the methanogenesis is preceded by a separate acidogenic stage.

7. The process according to claim 1 wherein the hydraulic retention time in the enclosed tank or lagoon is from 5 to 15 days.

8. The process according to claim 1 wherein the at least one micronutrient is selected from the group consisting of iron, cobalt, nickel, vitamins and selenium.

9. The process according to claim 1 wherein the monitoring of the at least one micronutrient is by ICP mass spectroscopy.

10. The process according to claim 1 further comprising, collecting solid struvite ($NH_4MgPO_4.6H_2O$) from the liquid output.

11. The process according to claim 10 wherein carbon dioxide is evolved from the liquid output to obtain the solid struvite.

12. The process according to claim 11 wherein the liquid output is filtered or subjected to a hydrocyclone process in order to isolate the solid struvite from the liquid output.

13. The process according to claim 11 wherein the liquid output following struvite removal is further processed by concentration of the liquid or evaporation to a solid product comprising nitrogen, phosphorus, and potassium.

14. The process according to claim 10 wherein the liquid output is conveyed along flexible tubing or piping, in order to prevent or minimize struvite from building up on an inner surface of a pipe or tube.

15. A process for the anaerobic digestion of a substantially aqueous solution or an aqueous and oil two phase system containing organic material to produce a liquid output wherein the COD is reduced by more than 70% from the input COD, consisting essentially of:

providing a feed of a substantially aqueous solution or aqueous and oil two phase system that has a COD concentration of 40 to 130 $kg/m^3$ to an enclosed tank or lagoon containing a sludge bed of methanogenic microorganisms via an upward flow;

subjecting the substantially aqueous solution, or aqueous and oil two phase system to methanogenesis to produce methane by digestion of the organic material in the enclosed tank or lagoon, wherein the liquid output from the enclosed tank or lagoon is not recycled in the process;

producing a liquid output from the enclosed tank or lagoon with a COD reduced by more than 70% from the input COD;

monitoring the content of at least one micronutrient in the feed and in the liquid output; and adding the at least one micronutrient when the difference in micronutrient level between the feed and the liquid output is less than expected based on the amount of methane produced and the expected growth of the methanogenic microorganisms.

* * * * *